United States Patent [19]

Ackerman et al.

[11] Patent Number: 5,220,014
[45] Date of Patent: Jun. 15, 1993

[54] RRNA SPECIFIC OLIGONUCLEOTIDES

[75] Inventors: Eric J. Ackerman, Bethesda; Shailendra K. Saxena, Kensington, both of Md.

[73] Assignee: The United States of America as represented by the Secretary of the Department of Health and Human Services, Washington, D.C.

[21] Appl. No.: 435,022

[22] Filed: Nov. 13, 1989

[51] Int. Cl.$^5$ .................... C07H 17/00; C12P 21/06; C12N 15/00
[52] U.S. Cl. .................. 536/24.5; 435/69.1; 435/172.1
[58] Field of Search ................. 536/27–29; 435/69.1, 172.1

[56] References Cited

PUBLICATIONS

Ware, et al., Nucleic Acid Res. 11(22) 7795–7817, 1983.
Yuen-Ling Chan, et al Nucleic Acid Res. 11(22) 7819–7831, 1983.
K. Jayaraman et al., Selective inhibition of Escherichia coli protein synthesis ..., Proc. Natl. Acad. Sci., Mar. 1981, vol. 78, No. 3, pp. 1537–1541.
Shailendra K. Saxena et al., Shiga Toxin, Shiga-like Toxi II Variant, and Ricin ..., The Journal of Biological Chemistry, Jan. 5, 1989, vol. 264, No. 1, pp. 596–601.
Ackerman et al., α-Sarcin Causes a Specific Cut in 28 S rRNA when ..., The Journal of Biological Chemistry, Nov. 15, 1988, vol. 263, No. 32, pp. 17076–17083.
Rodney, J. Y. Ho et al., Target-sensitive Immunoliposomes as an Efficient Drug Carrier for Antiviral Activity* vol. 262, No. 29, Issue of Oct. 15, pp. 13973–13978, 1987.
Chu, B. C. F. et al. "Ligation of oligonucleotides to nucleic acids or proteins via disulfide bonds" Nucleic Acid Research (1988) 16:3671–3691.
"Double-Agents Heterobifunctional Cross-Linkers Reactivity and Application Guide" Pierce Catalogue, pp. E-8-E-38.
Lewis, R. V. et al. "Photoactivated Heterobifunctional Cross-Linking Reagents Which Demonstrate the Aggregation State of Phospholipase A$_2$" Biochemistry (1977) 16:5650–5654.
Ji, T. H. et al. "Macromolecular Photoaffinity Labeling with Radioactive Photoactivable Heterobifunctional Reagents" Analytical Biochemistry (1982) 121:286–289.
Wollenweber, H-W. et al. "Synthesis and Biochemical Characterization of a Photoactivatable, Iodinatable, Cleavable Bacterial Lipopolysaccharide Derivative" The J. of Biological Chemistry (1985) 260:15068–15074.
Sorensen, P. et al. "Identification of the Interleukin-3 Receptor Using an Iodinatable, Cleavable Photoreactive Cross-Linking Agent" The J. of Biological Chemistry (1986) 261:9094–9097.
Shephard, E. G. et al. "The Use of Sulfosuccinimidyl-2-(p-azidosalicylamido)-1,3-dithiopropionate as a Cross-Linking Reagent to Identify Cell Surface Receptors" Analytical Biochemistry (1988) 168:306–313.
Goodchild, J. "Conjugates of Oligonucleotides and Modified Oligonucleotides: A Review of Their Synthesis and Properties" Bioconjugate Chemistry (1990) 1:165–187.

Primary Examiner—John W. Rollins
Attorney, Agent, or Firm—Cushman, Darby & Cushman

[57] ABSTRACT

The present invention relates to a method of inhibiting protein synthesis comprising contacting 28S rRNA of a protein synthesizing system with a protein synthesis inhibitory amount of an oligonucleotide that hybridizes to the -sarcin recognition domain loop of said 28S rRNA under condition such that hybridization occurs. The invention also relates to oligonucleotides suitable for use in such a method.

9 Claims, 7 Drawing Sheets

28S RNA

Positions of Control Oligonucleotides in *Xenopus* 28S rRNA.

FIG. 7

| α-Sarein Domain Oligo # | Sequence (5' to 3') | Position In Xenopus 28S rRNA |
|---|---|---|
| S.D. 1 | GTT CTT CTC GTA CT (14-mer) | 3726-3739 |
| S.D. 2 | GGT TCC TCT CGT ACT (15-mer) | 3726-3740 |
| S.D. 3 | CGT TCC TCT CGT ACT G (16-mer) | 3725-3740 |
| S.D. 4 | CGG TCC CTC TCG TAC TG (17-mer) | 3725-3741 |
| S.D. 5 | CGG TTC CTC TCG TAC TGA (18-mer) | 3724-3741 |
| S.D. 6 | CGG TTC CTC TCG TAC TGA G (19-mer) | 3723-3741 |
| S.D. 7 | CGG TTC CTC TCG TAC TGA GC (20-mer) | 3722-3741 |
| S.D. 8 | CTG AAC CTG CGG TTC CTC TCG TAC TGA GCA GGA TTA C (37-mer) | 3714-3750 |

RRNA SPECIFIC OLIGONUCLEOTIDES

BACKGROUND OF THE INVENTION

1. Field of the Invention

The present invention relates to oligonucleotides which hybridize to a region of ribosomal RNA (rRNA), particularly to such oligonucleotides which inhibit protein synthesis.

2. Background of the Invention

DNA oligonucleotides that are complementary to specific messenger RNAs (mRNA) have been used to inhibit synthesis of cellular and viral proteins. These complementary oligonucleotides, commonly known as antisense oligonucleotides, inhibit the translation of specific mRNAs by annealing to the mRNA and preventing formation of the directed protein.

Though there are many examples in the literature of oligonucleotides complementary to mRNAs, reports of the use of oligonucleotides complementary to specific ribosomal RNA (rRNA) sequences to affect protein synthesis are limited. Jayaraman et al. (Proc. Natl. Acad. Sci. USA, 78: 1537–1541, (1981)) have shown the inhibition of bacterial protein synthesis with oligonucleotides complementary to a region of 16S rRNA. However in their paper only a limited number of their complementary oligonucleotides were able to inhibit protein synthesis. Of those affecting protein synthesis only one showed any ability to affect transformed human cells and that oligonucleotide was only able to reduce protein synthesis by 10%.

α-Sarcin is a toxin that attacks the α-sarcin recognition domain in 28S rRNA. The α-sarcin recognition domain is a 14 nucleotide region found, for example, in yeast (Georgier et al., Nucleic Acids Res. 9, 6935–6952, (1981)), Xenopus (Ware et al., Nucleic Acids Res. 11, 7795–7817, (1983)) and rat (Chan et al., Nucleic Acids Res. 11, 7819–7831, (1983)). It is part of a putative 17 nucleotide loop approximately 400 nucleotides from the 3' end of the 28S rRNA (Clark et al., Nucleic Acids Res., 12, 6197–6220, (1984)).

This universally conserved loop of the α-sarcin domain is accessible to elongation factors EF-G and EF-Tu (MoaZed et al., Nature 334, 334–362, (1988)) as well as a group of toxins. Besides α-sarcin, this group of toxins includes ricin, Shiga toxin and Shiga-like toxin II which are specific N-glycosidases for both deproteinized 28S rRNA and 28S rRNA in isolated rat ribosomes. These toxins specifically remove the adenosine adjacent to the α-sarcin cut site (Endo et al., J. Biol. Chem. 262, 8128–8130, (1987); and Endo et al., Eur. J. Biochem. 171, 45–50, (1988)) and thereby inhibit protein synthesis (Ackerman et al., J. Biol. Chem. 263, 17076–17083, (1988) and Saxena st al., J. Biol. Chem. 264, 596–601, (1989)).

Toxin specificity and sites of nucleotide cleavage in the α-sarcin recognition domain loop of 28S rRNA in living cells was determined by the present inventors (Ackerman et al., J. of Biol. Chem. 263, 17076–17083, (1988) and Saxena et al., J. of Biol. Chem. 264, 596–601, (1989)). It was shown that the toxins α-sarcin, ricin, Shiga toxin and Shiga-like toxin inhibit protein synthesis in intact Xenopus oocytes by attacking specific nucleotides within the α-sarcin loop in 28S rRNA. α-Sarcin specifically cuts 28S rRNA 377 nucleotides from its 3' end; and ricin, Shiga toxin and Shiga-like toxin specifically remove adenine-3732 which is located 378 nucleotides from the 3' end of 28S rRNA.

Henderson and Lake (Proceedings of the 16th FEBS Congress, Part B, VNU Science Press, 219–228, (1985)) reported 50S ribosomal subunit collapse initiated by hybridization of a 14-base cDNA probe to the α-sarcin domain of *Escherichia coli* (*E. coli*) 23S rRNA. Using the same binding buffer and a synthetic 14-mer, White et al. (Nucleic Acids Res. 16, 10817–10831, (1988)) Were unable to hybridize the probe to the α-sarcin domain of intact 50S subunits. Furthermore, White et al. showed that subunit collapse was induced by binding buffer lacking the oligonucleotide. Thus attempts at simulating toxin inhibition of protein synthesis using oligonucleotides have been unsuccessful.

SUMMARY OF THE INVENTION

It is an object of the present invention to provide an oligonucleotide which hybridizes to the α-sarcin recognition domain loop of the large subunit of rRNA thereby inhibiting protein synthesis.

In one embodiment, the present invention relates to an oligonucleotide which hybridizes to rRNA and thereby inhibits protein synthesis.

In another embodiment, the present invention relates to an oligonucleotide which hybridizes to at least the conserved nucleotide sequence of the α-sarcin recognition domain loop of the large subunit of rRNA and thereby inhibits protein synthesis. The hybridized oligonucleotide covers the conserved nucleotides of the α-sarcin recognition domain loop of rRNA and may extend beyond the conserved nucleotide sequence in either or both directions.

In a further embodiment, the present invention relates to a method of inhibiting protein synthesis by contacting the large subunit of rRNA of a protein synthesizing system with a protein synthesis inhibitory amount of an oligonucleotide of up to 45 nucleotides in length under conditions such that hybridization to α-sarcin recognition domain of the rRNA is effected. The result would thereby render said rRNA nonfunctional in protein synthesis. The oligonucleotide may be linked to a cell or HIV-infected cell specific antibody for delivery. The protein synthesis system which is inhibited may be functioning in a tumor cell.

Various other objects and advantages of the present invention will become obvious from the drawings and the detailed description of the invention.

All publications mentioned herein are hereby incorporated by reference.

BRIEF DESCRIPTION OF THE DRAWINGS

FIG. 7 shows the oligonucleotides complementary to the α-sarcin recognition domain loop of 28S rRNA that were tested for the ability to inhibit protein synthesis in Xenopus oocytes.

DETAILED DESCRIPTION OF THE INVENTION

Figure 1:
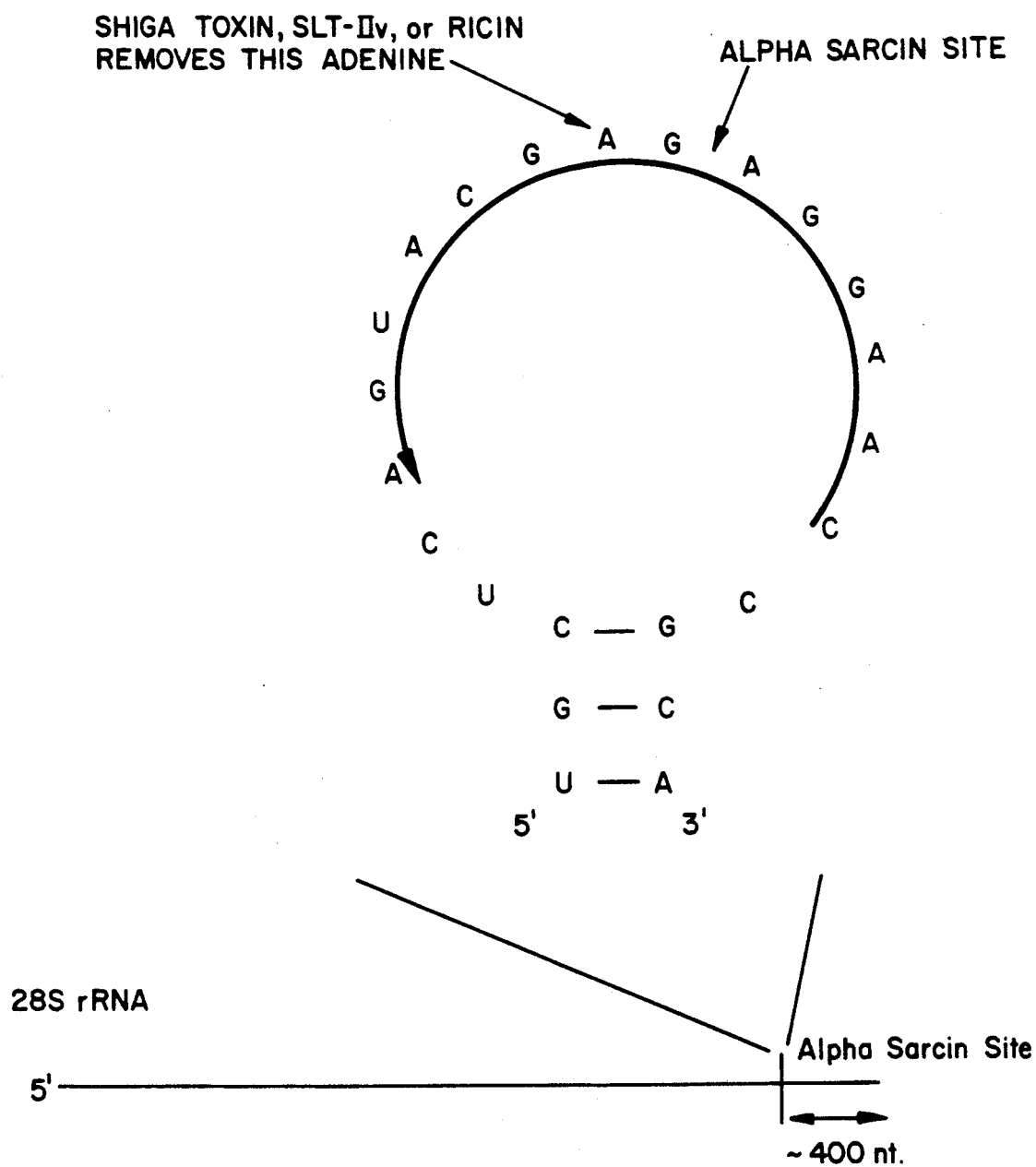
FIG. 1 shows the cleavage sites for α-sarcin, Shiga toxin, Shiga-like toxin IIv and ricin toxins. The semi-circled arrow inside the α-sarcin loop identifies the evolutionary conserved 14 nucleotides comprising the α-sarcin domain.

The present invention relates to oligonucleotides that hybridize to the α-sarcin loop of the large subunit of rRNA thereby blocking protein synthesis in intact cells. The invention further relates to the use of such oligonucleotides in a method of effecting targeted cell killing.

The meaning of the term "oligonucleotides" as used herein refers to oligodeoxynucleotides which are chemically the same as natural DNA, modified synthetic oligodeoxynucleotides which have no natural counterpart such as phosphorothioate oligodeoxynucleotides (Sproat et al., Nucleic Acids Research 17, 3373-3386, (1989) and references therein), oligoribonucleotides whcih are chemically the same as natural RNA, and modified oligoribonucleotides which have no natural counterpart such as 2'-O-methyloligoribonucleotides and tetrabiotinylated derivatives (Sproat et al., Nucleic Acids Research 17, 3373-3386, (1989)). The modified oligodeoxynucleotides and modified oligoribonucleotides have the advantage of being resistant to nucleases digestion which increases their ability to abolish protein synthesis in their target cells. Oligoribonucleotides also have the advantage of linking to antibodies more easily than oligodeoxynucleotides.

In one embodiment, an oligonucleotide of the present invention is linked to an antibody specific for a certain cell type. The antibody is used to deliver the oligonucleotide to the cell where the oligonucleotide would inhibit protein synthesis, thereby killing the cell.

The critical region of the large subunit of rRNA covered by the oligonucleotide of the present invention is the region that includes the conserved 14 nucleotide sequence -5' AGUACGAGAGGAAC 3'- of the α-sarcin recognition domain of the rRNA. The α-sarcin recognition domain loop is present in eucaryotes in 28S rRNA and in 23S rRNA in procaryotes, both of which are part of the large subunit of ribosomal RNA. Oligonucleotides extending beyond the 14 nucleotide sequence and covering up to about 12 additional nucleotides on the 5' end and up to about 11 nucleotides on the 3' end of the α-sarcin recognition domain loop of the large subunit of rRNA inhibit protein synthesis. It is preferable to use a 19-nucleotide long oligonucleotide which covers, in addition to the -5' AGUACGAGAGGAAC 3'- sequence of the α-sarcin recognition domain loop of the rRNA, three nucleotides on the 5' end and two nucleotides on the 3' end of the loop for inhibition of protein synthesis. Oligonucleotides which hybridize to this region stop protein synthesis and thus lead to cell death.

In the Xenopus oocyte the critical region corresponds to the nucleotide positions 3726-3739 extending up to positions 3714-3750 in the 28S rRNA. One skilled in the art will recognize that the numerical rRNA positions may vary from species to species depending on the overall size of the rRNA. Oligonucleotides which are sufficiently homologous to the α-sarcin recognition domain loops of different species to hybridize therewith will inhibit protein synthesis.

Exact complementarity between the oligonucleotide and the α-sarcin recognition domain loop of the large subunit of rRNA is not necessary. What is essential is that access to nucleotides in the critical region as defined by the present invention of Xenopus oocyte 28S rRNA or homologous positions in other species, be blocked by the oligonucleotide. Accordingly, the degree of complementarity between the large subunit of rRNA and the oligonucleotide need only be high enough to assure stable hybridization of the oligonucleotide chosen with the loop.

Stable hybrids can be formed under physiological conditions in the absence of secondary structure complications depending on the number of complementary base pairs and their composition (whether they are AT or GC base pairs). Therefore a longer oligonucleotide containing several mismatches can be as stable as a shorter perfectly matched oligonucleotide.

Due to the divergence in sequence of 23S and 28S rRNA beyond the conserved 14 nucleotides of the sarcin site, it is contemplated that oligonucleotides can be constructed which would specifically kill, for example, bacterial cells but not animals. The ability to construct oligonucleotides of the present invention that inhibit protein synthesis in a specific cell type will be useful in, for example, killing bacterial cells present in an animal while leaving protein synthesis in the animal cells unperturbed.

The present invention encompasses inhibition of protein synthesis in plants and animals due to the conservation of the α-sarcin recognition domain in the large subunit of rRNA between different species. The method of inhibiting protein synthesis disclosed herein can be used in procaryotes (for example bcateria), lower eucaryotes (for example, fungi) and higher eucaryotes (for example warm blooded animals, including mammals).

In a principal embodiment of the present invention, oligonucleotides complementary to the α-sarcin recognition domain loop of the large subunit of rRNA are delivered to tumor or infected cells. The oligonucleotide can be delivered to specific cells by means such as linking a targeting antibody to the oligonucleotides (Antibodies: A Laboratory Manual. Ed Harlow and David Lane (1988) Cold Spring Harbor Laboratory). By blocking protein synthesis, the oligonucleotides cause the diseased cell to be destroyed. Oligonucleotides are much less likely to provoke an antigenic response than other instruments now used to evoke cell death, such as toxins linked to antibodies, and thus are a potentially more effective means of killing diseased cells.

During the investigation which formed the basis of the present invention, oligonucleotides complementary to a segment of the large subunit of rRNA which prevent protein synthesis when hybridized to rRNA were identified. Oligonucleotides of varying lengths and degrees of complementary to the rRNA segment were injected into Xenopus oocytes to determine their ability to inhibit oocyte protein synthesis. Oligonucleotides fully covering the α-sarcin recognition domain of 28S rRNA or extending slightly beyond the domain inhibited protein synthesis.

The following non-limiting Examples, which are illustrative of the present invention, demonstrate the construction, selection, characterization and function of oligonucleotides complementary to α-sarcin recognition domain loop of 28S rRNA.

EXAMPLE 1

This example illustrates the construction and selection of oligonucleotides complementary to the α-sarcin recognition domain loop which inhibit protein synthesis.

Eight nucleotides of varying lengths from 14 to 37 nucleotides complementary to the α-sarcin loop, which is accessible to toxins in vitro and in vivo, were synthesized and injected into Xenopus oocytes. The oligonucleotides were synthesized with Applied Biosystems Models 381A and 380B DNA synthesizers. Oligonucleotides complementary to the α-sarcin domain (see FIG. 7) and control oligonucleotides complementary to other regions of 28S rRNA were used.

All oligonucleotides were tested for size and purity by gel electrophoresis. All oligonucleotides complementary to the α-sarcin domain are referred to with the prefix S.D. S.D. 6 was synthesized independently 3 times with different batches of reagents each time on 2 different DNA synthesizers to ensure that synthesis conditions were not responsible for causing inhibition of oocyte protein synthesis.

Twenty-30 nl samples of oligonucleotides at 1.4 mg/ml dissolved in H$_2$O were microinjected into the vegetal pole of mature stage VI Xenopus oocytes. All microinjection procedures were as described by Gurdon (Methods Cell Biol. 16, 125–139, (1977)).

At various times between 2 and 6 hours after the injection, the oocytes were incubated individually in 20 µl 1X Barth containing ~4 µCi L-[$^{35}$S]-Met for 16 hours as previously described (Ackerman et al., J. Biol. Chem. 263, 17076–17083, (1988)). The L-[$^{35}$S]-Met (1134 Ci/mmol) was from NEN.

To determine oocyte cytoplasmic protein synthesis, each oocyte was transferred after incubation and washed several times in 1X Barth before homogenization as previously described (Melton, Proc. Natl. Acad. Sci. USA 82, 144–148, (1985)). Every experiment included H$_2$O-injected and uninjected control oocytes. Total protein synthesis from these two controls was determined by TCA precipitation and electrophoresis-/autoradiography of labeled protein aliquots as previously described (Ackerman et al., J. Biol. Chem. 263, 17076–17083, (1988); Saxena et al., J. Biol. Chem. 264, (1989)). No data were retained unless these 2 controls produced identical total protein synthesis. Every experiment used oocytes obtained from different frogs in order to minimize any effects dependent upon oocytes from a particular frog.

Figure 2:
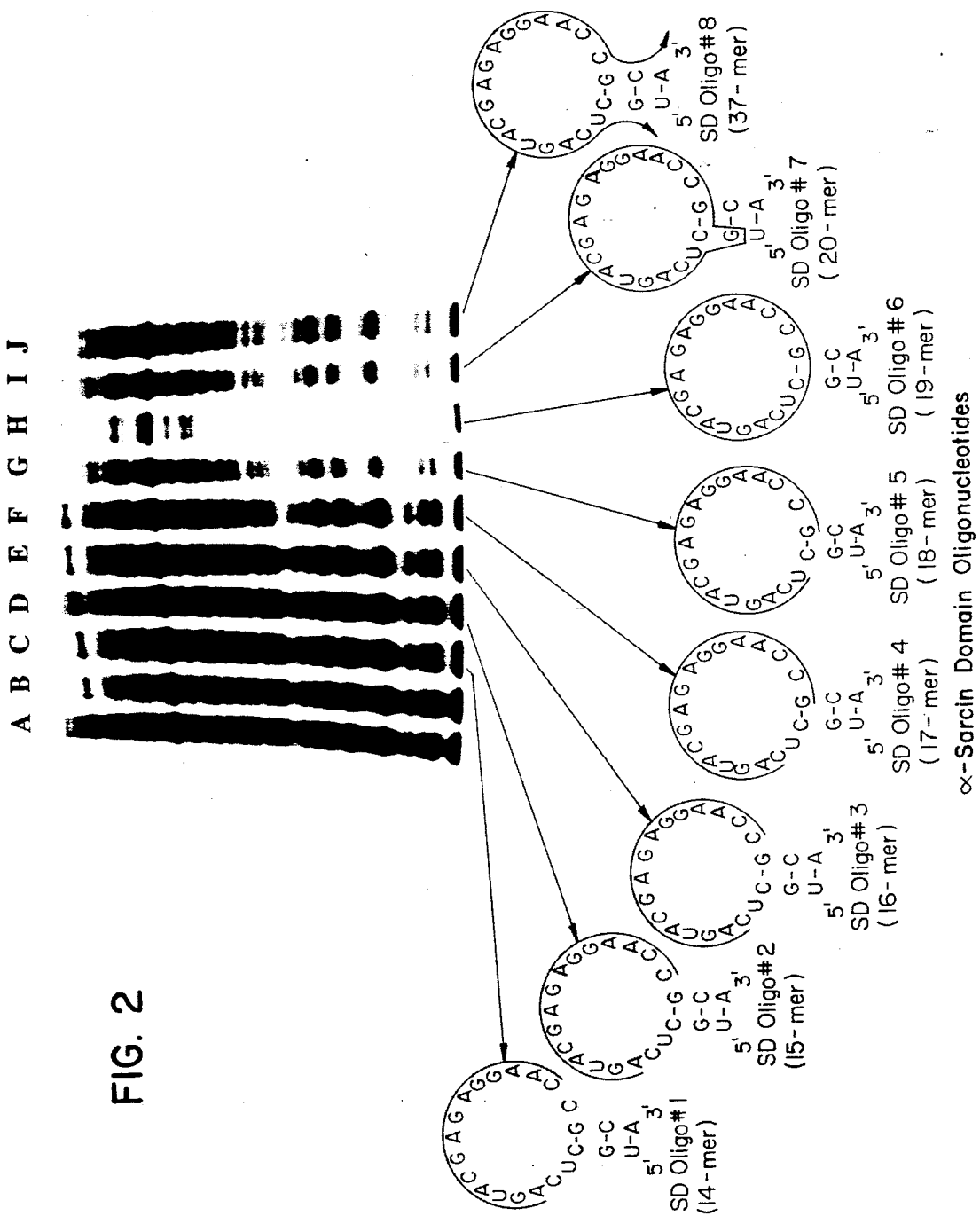
FIG. 2 demonstrates labeled protein synthesized in oocytes with no injection in lane A, H$_2$O injection in lane B and sarcin domain oligonucleotides 1–8 injection in lanes C–J, respectively.

No inhibition was observed for S.D. oligos #1–4, which only partially covered the sarcin loop; but injected S.D. oligos #5–8 did inhibit oocyte protein synthesis as shown in FIG. 2.

Maximal inhibition occurred for S.D. 6, a 19 nucleotide oligonucleotide, which fully covered the α-sarcin loop and the first C:G base pair of the stem. Quantitative TCA precipitations showed that more than 90% of cytoplasmic protein synthesis was eliminated by the oligonucleotide S.D. 6.

EXAMPLE 2

This example illustrates the dependency of protein synthesis inhibition on oligonucleotide concentration.

Figure 3:
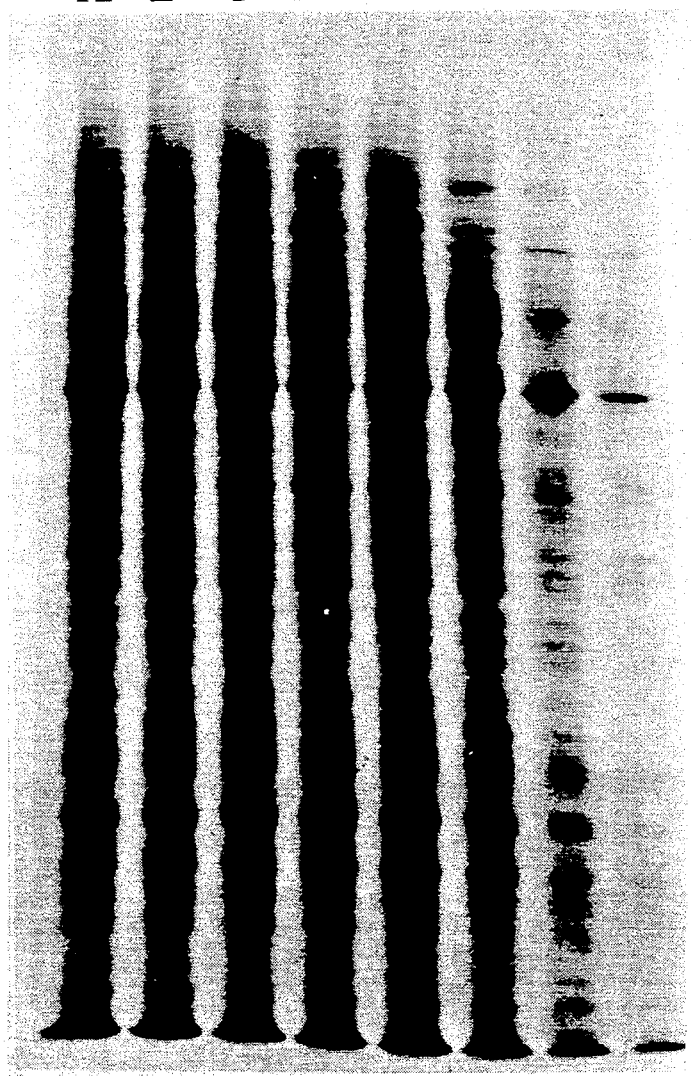
FIG. 3 demonstrates labeled protein synthesized in oocytes with no injection in lane A; H$_2$O injection in lane B; control oligonucleotide #1 injection at 0.2 mg/ml in lane C, 0.7 mg/ml in lane D and 1.4 mg/ml in lane E; and α-sarcin domain oligonucleotide injections at 0.2 mg/ml in lane F, 0.7 mg/ml in lane G and 1.4 mg/ml in lane H.
Figure 4:
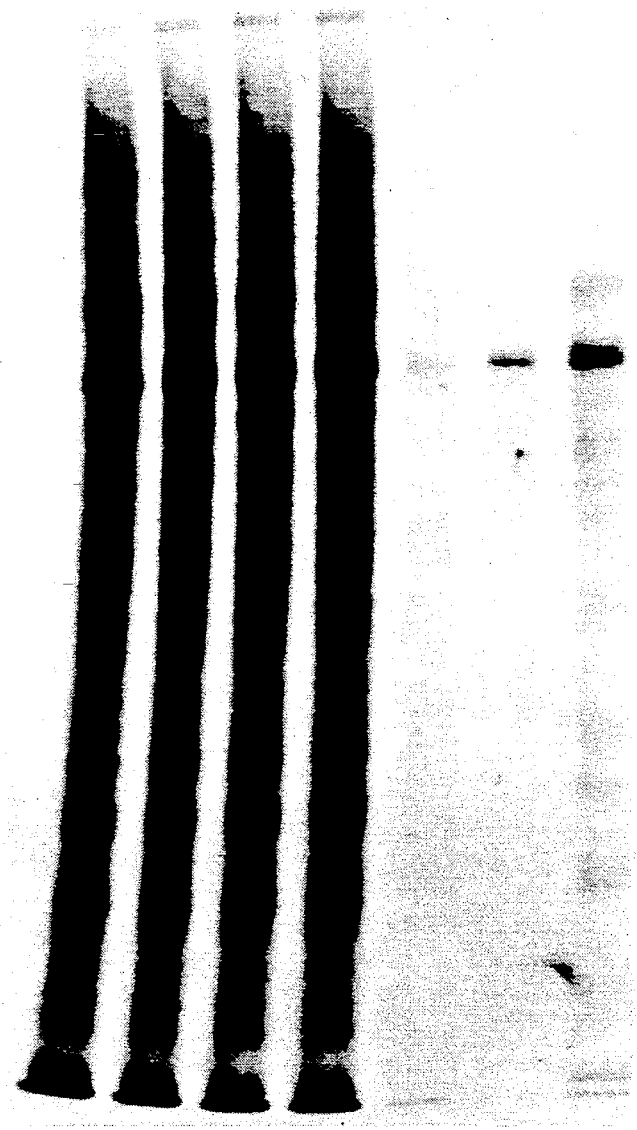
FIG. 4 demonstrates the inhibition of protein synthesis by cycloheximide and ricin. The oocytes were injected with ~20-30 nl of the following: lane A no injection, lane B H₂O injection, lane C injection of 1.4 mg/ml of control oligonucleotide #1, lane D injection of 1.4 mg/ml of control oligonucleotide #9, lane E injection of 0.1 mg/ml of ricin, lane F injection of 1.4 mg/ml of α-sarcin domain oligonucleotide α6, and lane G injection of 10 mg/ml of cycloheximide.

As oligonucleotide S.D. 6 was most effective at inhibiting oocyte protein synthesis, various concentrations, 0.2, 0.7 and 1.4 mg/ml, of this oligonucleotide and control oligonucleotide #1 were injected into oocytes to determine the maximal concentration for inhibition (see FIG. 3). No inhibition was observed with any concentration of control oligonucleotide #1 (FIG. 3, lanes C–E). Maximal inhibition with S.D. 6 occurred at an injection concentration of 1.4 mg/ml or ~2×10$^{12}$ molecules/oocyte or 8.9 µM in the oocyte (see FIG. 3, lane H). Without considering the stability of injected oligonucleotide, this number is comparable to the concentration of cycloheximide required for similar inhibition of oocyte protein synthesis (see FIG. 4, lane G and FIG. 5, lane L). For similar inhibition of protein synthesis with Shiga toxin or ricin (Saxena et al., J. Biol. Chem. 264, 596–601, (1989)), a minimum of ~10$^7$ molecules/oocyte must be injected or 0.11 nM in the oocyte. In FIG. 4, lane E, ~10$^{10}$ molecules of ricin D per oocyte were injected.

EXAMPLE 3

This example illustrates the degree of exact complementarity needed between the oligonucleotide and the α-sarcin loop for the inhibition of protein synthesis.

As it was expected that S.D. oligonucleotides inhibited oocyte protein synthesis by at least a transient interaction with the sarcin domain, oligonucleotides containing a variety of mismatches at either or both of the critical positions attacked by toxins were injected into oocytes to test their ability to inhibit oocyte protein synthesis.

Figure 5:
FIG. 5 demonstrates the ability the oligonucleotides containing mismatches to the α-sarcin domain to inhibit oocyte protein synthesis. 20-30 nl of the following was injection into oocytes: lane A no injection, lane B H₂O injection, lane C α-sarcin domain oligonucleotide #6 [no mismatches] at 1.4 mg/ml injection, lane D-K α-sarcin domain oligonucleotides at 1.4 mg/ml containing the indicated mismatches in bold letters below the lanes injection and lane L cycloheximide at 1.4 mg/ml injection. The * in the α-sarcin domain identifies the adenine removed by ricin and Shiga toxin and the arrow denotes the cleavage site for α-sarcin in Xenopus oocytes.
Figure 5:
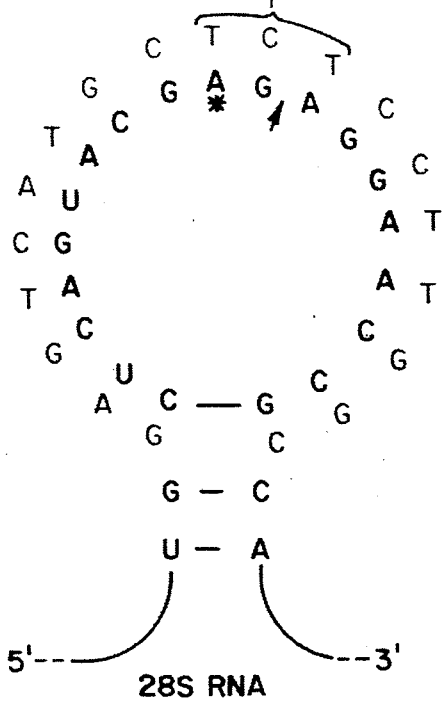

S.D. 6 oligonucleotides containing the 3 possible mismatches to the adenine removed by ricin, Shiga toxin and SLT-II are all as effective as native S.D. 6 (see FIG. 5, lanes C, D, E and F). S.D. 6 oligonucleotides containing the 3 possible mismatches at the quanine position cleaved by α-sarcin are less effective inhibitors of oocyte synthesis (see FIG. 5, lane G, H and I); but are comparable to cycloheximide injected at an identical concentration (see FIG. 5, lane L). S.D. 6 oligonucleotides containing mismatches at both positions as well as the adjacent 3' adenosine also inhibit oocyte protein synthesis (see FIG. 5, lanes J and K respectively). Therefore, the specific sequence covered by the oligonucleotide is more important than exact complementarity between the oligonucleotide and the 28S rRNA.

EXAMPLE 4

This example illustrates the specificity of oligonucleotide-induced inhibition of protein synthesis.

Oligonucleotides complementary to 9 other regions of the Xenopus 28S rRNA were injected into oocytes and examined for their ability to inhibit protein synthesis. Three of the oligonucleotides were complementary to potential loop structures in 28S rRNA. Six of the oligonucleotides were complementary to potential stem or stem/loop structures. Binding sites for these oligonucleotides covered several different regions of 28S rRNA.

Figure 6A:
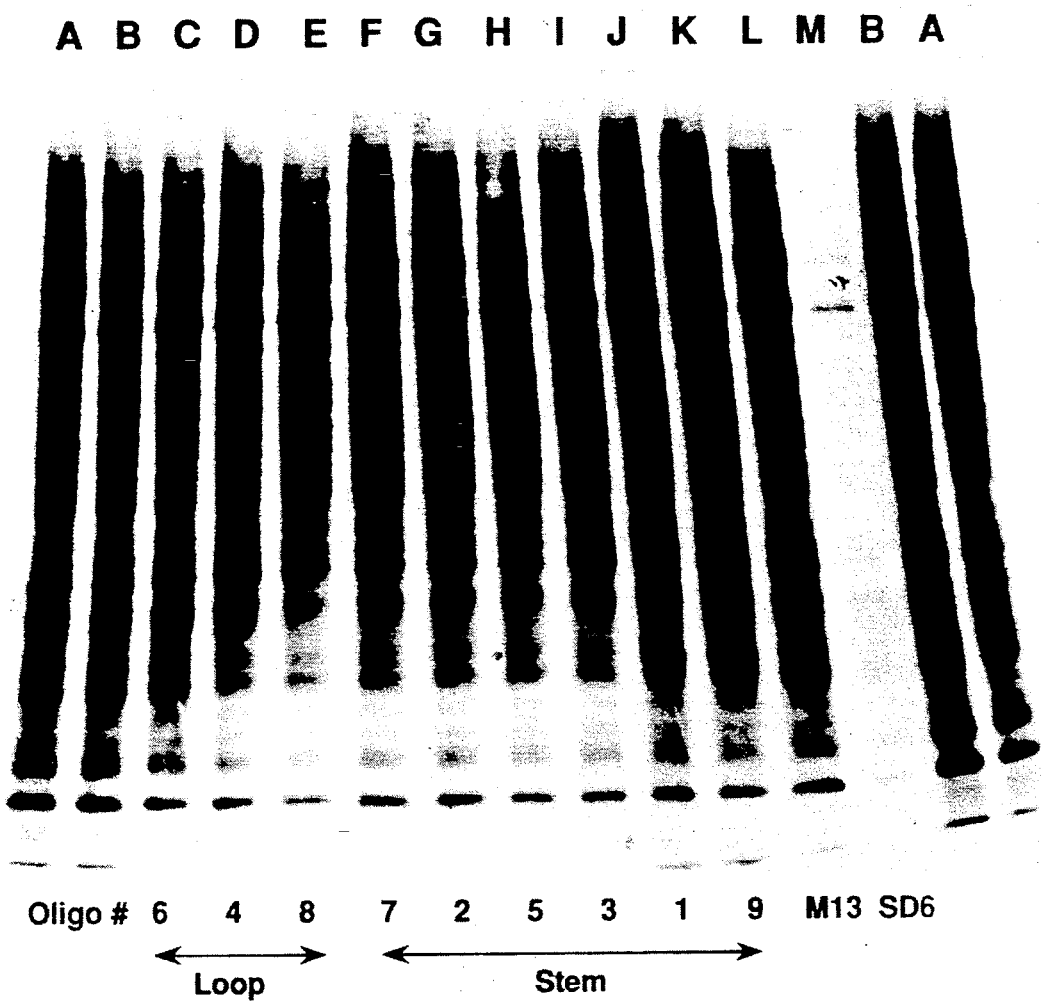
FIG. 6A demonstrates that injected oligonucleotides complementary to regions of Xenopus 28S rRNA other than the α-sarcin domain do not inhibit protein synthesis.
Figure 6B:
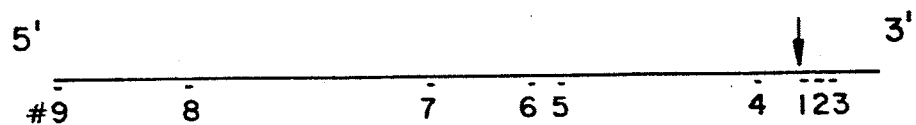
FIG. 6B shows the positions of control oligonucleotides in xenopus 28 SrRNA.

None of the 9 control oligonucleotides inhibited oocyte protein synthesis as shown in FIG. 6. The Pharmacia M13 universal sequencing primer (17 nucleotides in length) also had no effect on protein synthesis. Only the oligonucleotide which spanned the α-sarcin loop, S.D. 6, inhibited oocyte protein synthesis. TCA precipitation of total protein synthesis showed no appreciable difference between uninjected or H$_2$O-injected oocytes and the 9 control oligonucleotides.

EXAMPLE 5

This example illustrates secondary structure of the oligonucleotides.

The sequences of all the oligonucleotides used here as well as the sequence of the α-sarcin loop were analyzed with the computer program Fold (Zuker et al., Nuclei Acids. Res. 9, 133-148, (1981)) provided with the University of Wisconsin Genetics Computer Group software package, version 5.0.

All the sequences analyzed can be folded into various structures. For example, the α-sarcin loop depicted in FIG. 1 can be drawn with a shortened loop containing two additional base pairs. If G:T base pairing is allowed, all of the sarcin domain oligonucleotides can be folded into stem loop structures containing stems with 3 or 4 uninterrupted base pairs.

Although S.D. 8 (37 nucleotides in length) covers the same regions of the α-sarcin loop as S.D. 6 (19 nucleotides in length), S.D. 6 inhibits oocyte protein synthesis more effectively than S.D. 8. One possible explanation is that S.D. 8 may fold into a stable secondary structure containing 10 base pairs, although these base pairs are interrupted by several mismatches.

All of the nine control oligonucleotides used have numerous possible secondary structures. The two most stable stem-loop structures occur for control oligonucleotides 3 and 5, which contain 9 and 8 uninterrupted G:C base pairs, respectively. However, no significant stems exist for the other control oligonucleotides. Therefore, potential intramolecular secondary structures do not explain the contrasting effects on protein synthesis between sarcin domain oligonucleotides and the controls.

While the foregoing invention has been described in some detail for purposes of clarity and understanding, it will be clear to one skilled in the art from a reading of this disclosure that various changes in form and detail can be made without departing from the true scope of the invention.

What is claimed is:

1. An oligonucleotide of up to 45 nucleotides in length which hybridizes to the α-sarcin recognition domain loop of the large subunit of rRNA thereby rendering said rRNA nonfunctional in protein synthesis.

2. The oligonucleotide according to claim 1, wherein said oligonucleotide hybridizes to the sequence 5'-AGUACGAGAGGAAC-3'.

3. An oligonucleotide of up to 45 nucleotides in length which hybridizes to up to 12 nucleotides 5' of the sequence of the α-sarcin recognition domain loop of the large subunit of rRNA or up to 11 nucleotides 3' of said sequence of said loop, wherein hybridization of said oligonucleotide renders said rRNA nonfunctional in protein synthesis.

4. The oligonucleotide according to claim 3, wherein said oligonucleotide hybridizes to up to 3 nucleotides 5' of said sequence of said loop and up to 3 nucleotides 3' of said sequence of said loop.

5. The oligonucleotide according to claim 1 which is S.D. 6 in FIG. 7.

6. The method of inhibiting protein synthesis comprising contacting the large subunit of rRNA of a protein synthesis system with a protein synthesis inhibitory amount of said oligonucleotide according to claim 1 under conditions such that hybridization is effected.

7. The method according to claim 6 wherein said oligonucleotide is coupled to cell specific antibody.

8. The method according to claim 6 wherein said protein synthesis system is present in a tumor cell.

9. The method according to claim 8 wherein oligonucleotide is linked to antibody specific for said tumor cell.

* * * * *